United States Patent
Burns et al.

[11] Patent Number: 5,876,121
[45] Date of Patent: Mar. 2, 1999

[54] SUBSTRATE TEMPERATURE MEASUREMENT BY INFRARED SPECTROSCOPY

[75] Inventors: David H Burns, Montreal; Frederic Series, Sillery, both of Canada

[73] Assignees: McGill University, Montreal; Universite Laval, Quebec, both of Canada

[21] Appl. No.: 776,580
[22] PCT Filed: Aug. 3, 1995
[86] PCT No.: PCT/CA95/00466
§ 371 Date: Jun. 30, 1997
§ 102(e) Date: Jun. 30, 1997
[87] PCT Pub. No.: WO96/04535
PCT Pub. Date: Feb. 15, 1996

[30] Foreign Application Priority Data

Aug. 5, 1994 [GB] United Kingdom .................. 9415869

[51] Int. Cl.⁶ .............................. G01K 11/00; G01J 5/00
[52] U.S. Cl. .............................. 374/161; 374/121; 356/43
[58] Field of Search .................................. 374/161, 121; 250/339.04; 356/43

[56] References Cited

U.S. PATENT DOCUMENTS

| | | | |
|---|---|---|---|
| 4,016,761 | 4/1977 | Rozzell et al. | 374/161 |
| 4,176,552 | 12/1979 | Hammer | 374/161 |
| 4,402,311 | 9/1983 | Hattori | 600/117 |
| 4,523,092 | 6/1985 | Nelson | 374/161 X |
| 4,575,259 | 3/1986 | Bacci et al. | 374/161 X |
| 4,659,234 | 4/1987 | Brouwer et al. | 374/121 |
| 4,703,175 | 10/1987 | Salour et al. | 374/161 X |
| 5,348,396 | 9/1994 | O'Rourke et al. | 374/161 |
| 5,352,038 | 10/1994 | Schmidt et al. | 374/161 X |
| 5,419,312 | 5/1995 | Arenberg et al. | 600/108 |
| 5,446,681 | 8/1995 | Gethner et al. | . |
| 5,455,177 | 10/1995 | Krause et al. | . |
| 5,553,613 | 9/1996 | Parker | 600/316 |

Primary Examiner—Elizabeth L. Dougherty
Assistant Examiner—Paul D. Amrozowicz
Attorney, Agent, or Firm—Swabey Ogilvy Renault

[57] ABSTRACT

The temperature of an infrared radiation scattering medium which contains water, for example, biological tissue and paper, cement and clay substrates, is determined by exposing the medium to infrared radiation, measuring the reflected radiation scattered by the medium, comparing the reflected radiation with calibrated values, and evaluating the temperature of the medium from the comparison; the technique provides a means of non-invasive determination of temperature in biological tissue which has utility in medical diagnosis.

11 Claims, 10 Drawing Sheets

FIG_4

SUBSTRATE TEMPERATURE MEASUREMENT BY INFRARED SPECTROSCOPY

This application is a 371 of PCT/CA 95/00466 filed Aug. 3, 1995.

TECHNICAL FIELD

This invention relates to determination of a parameter of a medium which scatters infrared radiation; in particular, it is concerned with a method and apparatus for determining the temperature of such a medium.

The invention has particular application to the determination of the temperature of biological tissue, but also has application to other media which contain water and which scatter infrared radiation, for example, substrates in paper, cement and clay product manufacture.

The invention is more especially concerned with a method and apparatus for quantitative, non-invasive bioenergetic measurement. Towards this end, a method and apparatus for determining tissue temperature is provided.

BACKGROUND ART

Tissue temperature is critical to cellular bioenergetics and can be useful clinically to locate blood perfused regions in diseased or inflamed tissue. Clinical use of tissue temperature or thermography has been limited by uncertainties in temperature measurement. The most common method for temperature measurement is to use invasive microelectrodes or thermocouples. However, these probes have several disadvantages, including: tissue damage, alterations of tissue temperature and single point detection. Measurement of tissue temperature using emitted light in the infrared or microwave region has overcome many of the disadvantages of electrode measurements. Assuming the tissue is a blackbody radiator, noninvasive images of tissue are possible using infrared emission. However, the extremely high extinction coefficients for the infrared wavelengths in wet tissue result in light penetration of a few hundred microns or less. For wet tissue such as the lung or gut, this penetration depth is not sufficient. Likewise, infrared light is not easily coupled into fiber optic systems for endoscopic or bronchoscopic measurements.

U.S. Pat. No. 5,262,644, J. F. Maguire describes a method and apparatus for providing spectroscopic information remotely using incident radiation, a detector and fiber optic coupling; it is indicated that the temperature of a sample may be deduced from the intensity difference between the Stokes and anti-Stokes lines by application of the Boltzmann relationship to the intensity difference.

DISCLOSURE OF THE INVENTION

The present invention employs measurements of the reflectance infrared spectra from a specimen, especially the near-infrared spectra. Temperature dependent changes in the hydrogen bonding of water within the specimen, for example tissue, results in change of the reflectance spectra. Using sets of specimen measurements with known temperature, a calibration equation is determined by statistical analysis of the data. Computer simulations and infrared, especially near-infrared, measurements of known phantoms are used to evaluate the sensitivity of the method for studies of specimens with different scattering properties. The system provides a new tool to study local specimen temperature thereby providing a means for rapid, non-invasive measurement of parameters, for example, parameters critical to bioenergetics in tissue for research and clinical use.

Thus in accordance with the invention there is provided a method of determining the temperature of an infrared radiation scattering medium comprising: exposing an infrared scattering medium containing a liquid which contains different hydrogen bonding at different temperatures to infrared radiation, measuring reflected infrared radiation scattered by the medium, comparing the reflected radiation with calibrated values of reflected radiation and temperature, and evaluating the temperature of the medium from the comparison.

In particular the radiation has a near-infrared wavelength between 700 nm and 2500 nm.

In particular reflected infrared radiation at different wavelengths is measured. In particular, the different wavelengths comprise wavelengths for water between 1100 and 1300 nm including a wavelength for free OH groups and a wavelength for hydrogen-bonded OH groups.

In another aspect of the invention there is provided an apparatus for determining the temperature of an infrared radiation scattering medium comprising: i) a plurality of optical fibers effective to transmit infrared radiation from a source to a scattering medium and to transmit reflected, scattered radiation from said scattering medium, ii) a source of infrared radiation operatively associated with said fibers for transmission of infrared radiation, iii) detector means adapted to receive reflected radiation for multiple wavelengths from said optical fibers and issue signals responsive thereto, and iv) evaluating means for receiving said signals and determining the temperature of the scattering medium therefrom, said evaluating means being adapted to compare the received signals with signals corresponding to calibrated values of reflected radiation and temperature.

Although the invention is not restricted to the use of near-infrared radiation, such radiation is preferred for non-invasive temperature measurements of biological tissue because absorption of light is low in this spectral region and non-invasive measurements can be made through intervening tissue. Furthermore, commercially available endoscopes transmit near-infrared radiation, but are not adapted to transmit mid or far-infrared radiation. Mid and far-infrared radiation are acceptable for other applications, particularly those involving surface measurements of temperature.

In particular, the optical fibers are associated with an endoscope, for example, a bronchoscope, a cystoscope or a gastroscope, effective for entry to the respiratory, urinary and gastrointestinal tracts respectively, whereby minimally invasive examination can be conducted, including visual observation and temperature determination of different specific sites of biological tissue, for example, lung tissue, in accordance with the invention.

Typically the endoscope will include an eyepiece for viewing the tissue or may include a camera linked to a television on which an image of the tissue can be viewed. In this way it is possible to view the tissue at different sites and, by means of the invention, determine the temperatures of such sites. Thus, for example, degree of inflammation may be assessed, not only by visual examination, but also, more precisely, by temperature determination.

The detector suitably comprises an infrared spectro photometer, preferably a multiwavelength near-infrared Fourier transform or dispersive spectro photometer or a spectrophotometer having filters adapted to separate the multiple wavelengths, the filters suitably being for hydrogen bonding wavelengths in the range of 900 to 1300, suitably 1100 to 1300 nm, more especially a first filter for a wavelength for free OH groups and a second filter for a wavelength for hydrogen-bonded OH groups.

Suitably the detector includes a diode array detector, or similar device, for issuing signals, particularly electrical pulses, based on the received or separated wavelengths. These signals are fed to a computer or equivalent device which permits comparison of the signals with an established relationship between wavelength and temperature for the tissue, whereby the temperature of a specific site can be evaluated. The procedure is repeated at different sites.

In particular embodiments the medium is a biological tissue, a paper substrate, cement or a clay substrate, but the invention may also be employed in conjunction with other water-containing media which scatter infrared radiation.

The invention has particular application in non-invasive medical diagnosis.

DESCRIPTION OF PREFERRED EMBODIMENTS

The calibration values may be determined for specimens at known temperature, and the development of such calibration values is well within the skill of persons in the art. The comparison values may be stored in comparison tables, or more conveniently in software which readily provide an evaluation of the temperature based on the measured scattered radiation and the comparison values.

The near-infrared wavelength region between 700 nm and 2500 nm has significant penetration into tissue and can be readily incorporated into fiber optic systems. The relatively short wavelength (high energy) of the near infrared as compared to the mid-infrared and microwave spectral region, show little blackbody emission and are unsuited for classic thermographic measurements.

Typically, in tissue the diffuse reflectance spectrum is dominated by the absorbance bands associated with the OH groups in water. There are many OH absorbances in the near-infrared region. Due to differences in hydrogen bonding, the spectrum of water will change at different temperatures. The near infrared spectral differences can be used to make an accurate temperature sensor of a pure non-scattering water sample with measurements within 0.1° C. being possible.

A temperature calibration using pure water will, however, not accurately measure temperature in tissue. This is due to the presence of additional absorbers in tissue along with tissue scattering. The present invention provides a means to calibrate temperature in tissue using water absorbance thereby providing a robust measure of temperature regardless of specimen composition or scattering properties. The invention is also applicable to media containing liquids other than water which contain different hydrogen bonding at different temperatures.

Information retrieval from broad, overlapping spectra is not trivial due to effects of interfering bands. Fundamental to successful statistical analysis is a valid training data set of spectra with quality factors that have been determined by independent reference methods. Equations relating the quality factors to the spectra of the training set are obtained by statistical regression techniques. The resulting transformation rules obtained by statistical regression analysis are subjected to validation using independently measured sets of samples. With successful verification, the transformation rule can then be used to derive predicted values of sample properties. Multivariate approaches overcome the problem of overlapping absorbances and allow simultaneous multi-property analysis.

There are two general approaches to the statistical regression analysis—1) methods that utilize full spectra for transformation such as partial least squares (H. Martens and S. A. Jensen, Partial Least Squares Regression: A New Two-Stage NIR Calibration Method. In Progress in Cereal Chemistry and Technology, Vol. 5a (J. Holas and J. Kratochvil, eds.), Elsevier, Amsterdam, 607:647, (1983)), PLS, or 2) methods that select individual wavelengths with the highest correlation coefficients for the quality factors, such as stepwise linear regression (I. Ben-Gera and K. H. Norris, J. Food Sci., 33:64 (1968)), SMLR. The SMLR methods are most appropriate for transformation of predictive equations to filter-based instrument designs, but PLS results give a somewhat better estimate of the overall information content of spectra.

In one embodiment of this invention analytical predictive equations are employed different from the approaches of prior methods. Prior methods perform various math treatments of spectra such as smoothing and/or derivative calculations prior to SMLR analysis. Analyses are carried out on these sets of smoothed and differentiated spectra. Combinations of wavelengths are sought which produce the highest regression coefficients with lowest standard errors of regression. Selected combinations of wavelengths are then used to predict values of test sets and final conditions are selected based upon standard errors of prediction. The result is that all wavelengths in the spectra have had the same math treatment. Thus SMLR methods produce prediction equations with filters all having the same bandwidths.

The method in the new embodiment is similar to the SMLR method, the result, particularly for the design of filter-based instrumentation, is quite different. The spectra are not preprocessed by smoothing, instead the untreated training sets are used to calculate optimal filters with varying center wavelengths and bandwidths. In this approach each predicted filter has an associated bandwidth which produces the most robust prediction. Thus the proposed method produces filter specifications optimized for the conditions of a filter spectrometer instead of filter specifications based on optimizing the original data acquisition and treatment procedures.

MODES OF CARRYING OUT THE INVENTION

Figure 1:
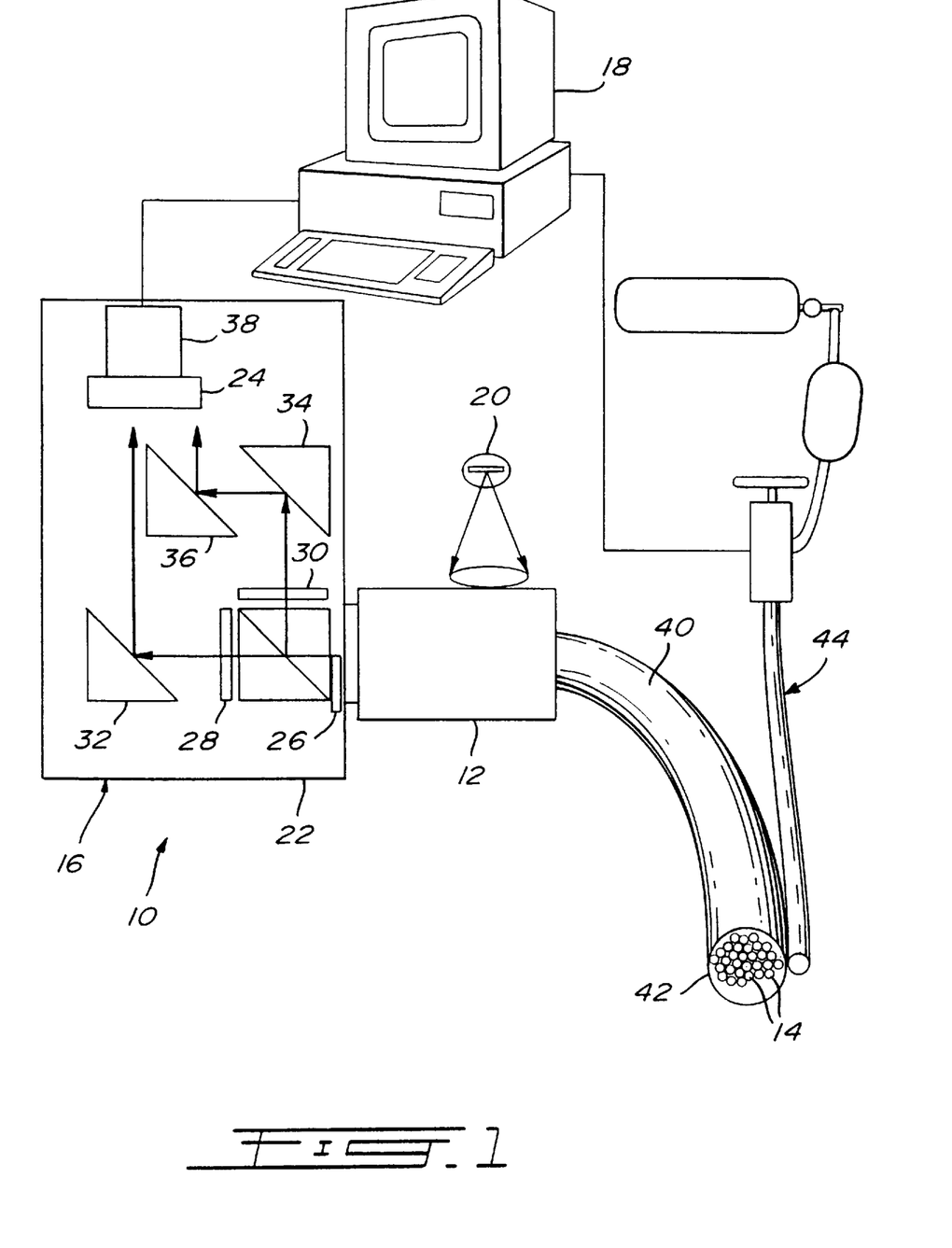
FIG. 1 illustrates schematically an apparatus in accordance with one embodiment of the invention.

With further reference to FIG. 1, apparatus 10 includes a bronchoscope 12 associated with a plurality of optical fibers 14, a detector 16, a computer 18 and a source 20 of radiation, for example, an intensity stabilized tungsten-halogen light.

Detector 16 includes a spectrophotometer 22 and a charge coupled detector array 24.

Spectrophotometer 22 includes a beam splitter 26 and filters 28 and 30 for different wavelengths. Mirrors 32, 34 and 26 reflect the beams of different wavelength from filters 28 and 30 to the array 24.

The detector 16 further includes a camera 38.

The fibers 14 are contained within a tubular housing 40 having a head 42 which may be cooled by a chiller 44.

In operation radiation, preferably near-infrared radiation is transmitted from source 20 to the bronchoscope 12 and passes along the optical fibers 14 from which it is delivered to a lung tissue site being investigated by the bronchoscope The fibers 14 may include separate fibers for delivery of transmitted radiation and return of reflected radiation, or the same fibers may serve both functions.

The radiation is reflected by the tissue at a site under investigation and is transmitted to spectrophotometer 22 where it is split by beam splitter 26 into two components. One component passes through filter 28 which isolates a wavelength associated with free OH groups of water in the tissue and the second component passes through filter 30 which isolates a wavelength associated with hydrogen-bonded OH groups of water in the tissue.

The wavelength passing filter 28 is reflected by mirror 32 and the reflected beam travels to array 24. The wavelength passing filter 30 is reflected by mirrors 34 and 36 and the reflected beam similarly travels to array 24.

The array 24 issues signals responsive to each of the reflected beams and these signals are recorded in computer 18 to generate an image. Computer 18 compares the signals with a previously established relationship between temperature and wavelength and provides a temperature result or image for each signal derived from such relationship.

This procedure is repeated for different sites of the lung tissue.

The reflected beams may also be fed through a camera 38 from which an image of the site under investigation can be developed.

As an alternative to measuring temperature, the rate of tissue rewarming can be evaluated; for this purpose a chiller 44 associated with the head 42 of the housing 40 of the fibers 14, cools the tissue at a site under investigation and the shift in wavelength as the temperature rises after the chilling effect is interrupted, is monitored.

The array 24 may, for example, be a photo diode array which produces an electrical pulse responsive to radiation received, from which electrical pulses on image can be obtained.

Figure 2:
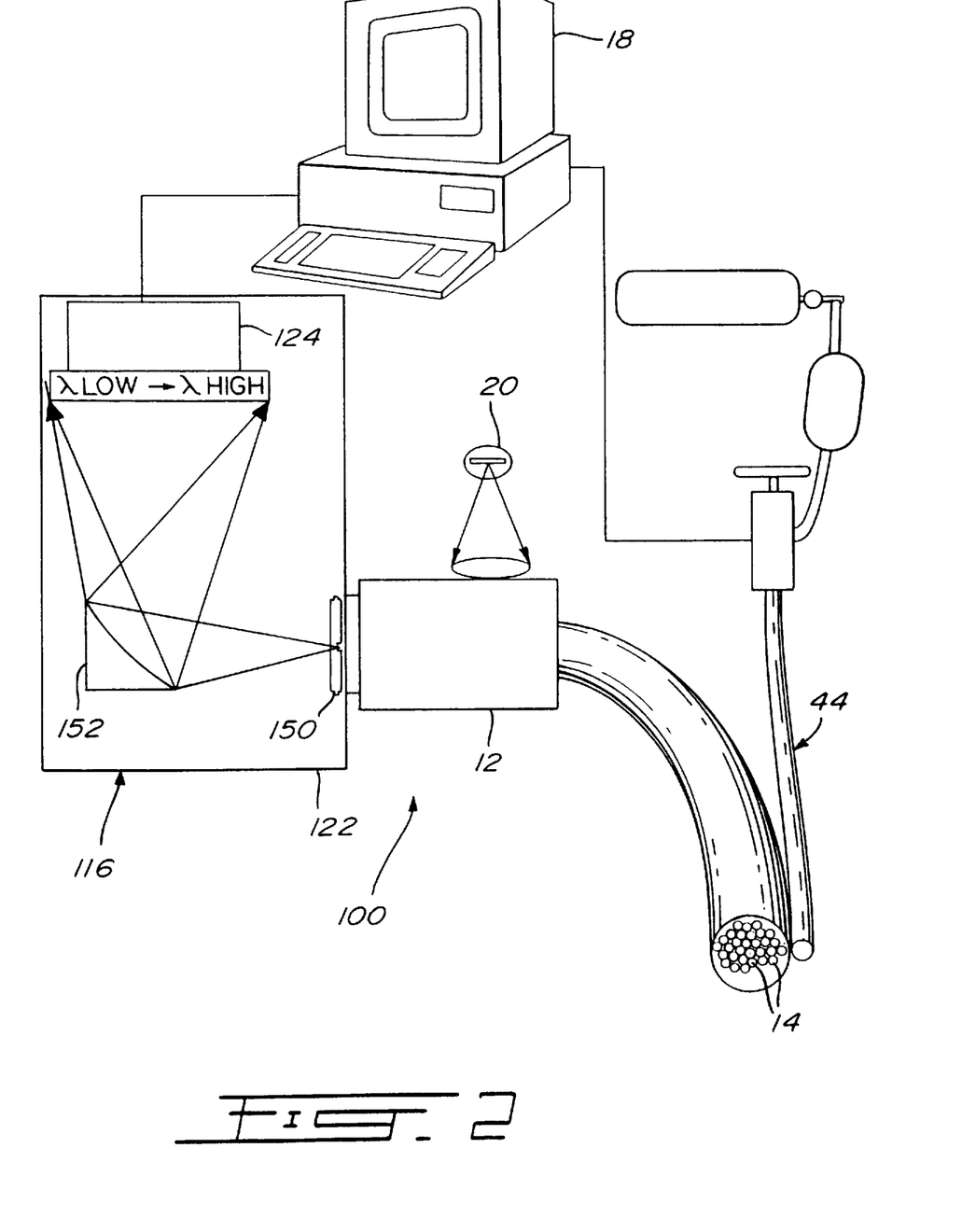
FIG. 2 illustrates schematically an apparatus in accordance with another embodiment of the invention.

With further reference to FIG. 2, apparatus 100 is similar to apparatus 10 of FIG. 1, and in so far as it employs the same components, the same identification integers are employed as in FIG. 1. Thus apparatus 100 includes bronchoscope 12, optical fibers 14, computer 18 and source 20 as well as chiller 44.

A detector 116 includes a spectrophotometer 122 and a photodiode array 124.

Within spectrophotometer 122 is housed an entrance slit 150 and a concave diffraction grating 152.

In use radiation is reflected by the tissue at a site under investigation and is transmitted to spectrophotometer 122 where it passes through entrance slit 150. The reflected radiation is diffracted into a range of wavelengths from low wavelength to high wavelength, in grating 152 and the thus diffracted or dispersed wavelengths are received by photodiode array 124 which issues a signal, more especially an electrical signal, responsive to individual wavelengths, which signals are fed to computer 18 as in FIG. 1.

EXAMPLES

Example 1 i) Instrumentation/Software

Spectral data was collected using a modified Nicolet 550 Fourier transform spectrometer. The system was controlled with a personal computer (AMT, 486–66 MHz). To provide sufficient signal-to-noise for temperature estimation, the signal from 128 scans was integrated in all of the measurements presented here. A custom temperature controlled sample holder was made to allow both transmission and scattering measurements. Reference temperature for the samples was measured using a Fluke M50 thermocouple detector. The detector is sensitive to 0.1° C.

The OMNIC data analysis package (Nicolet), was used to determine the calibration coefficients for thermal measurements. The major component used in the OMNIC package was the Partial Least Squares (PLS) regression routine.

ii) Results

Figure 3:
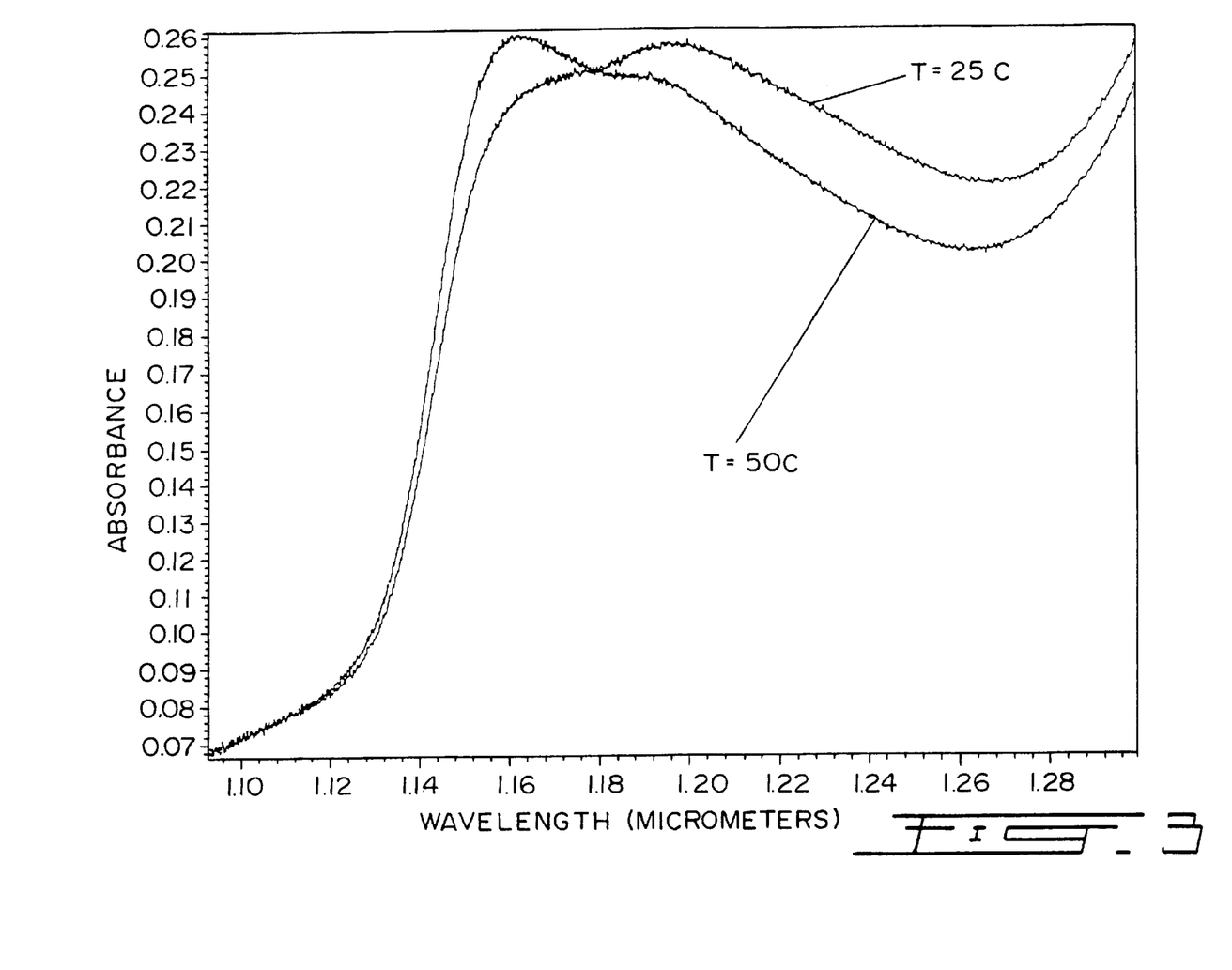
FIG. 3 shows near-infrared spectra for water at 25° C. and 50° C.
Figure 4:
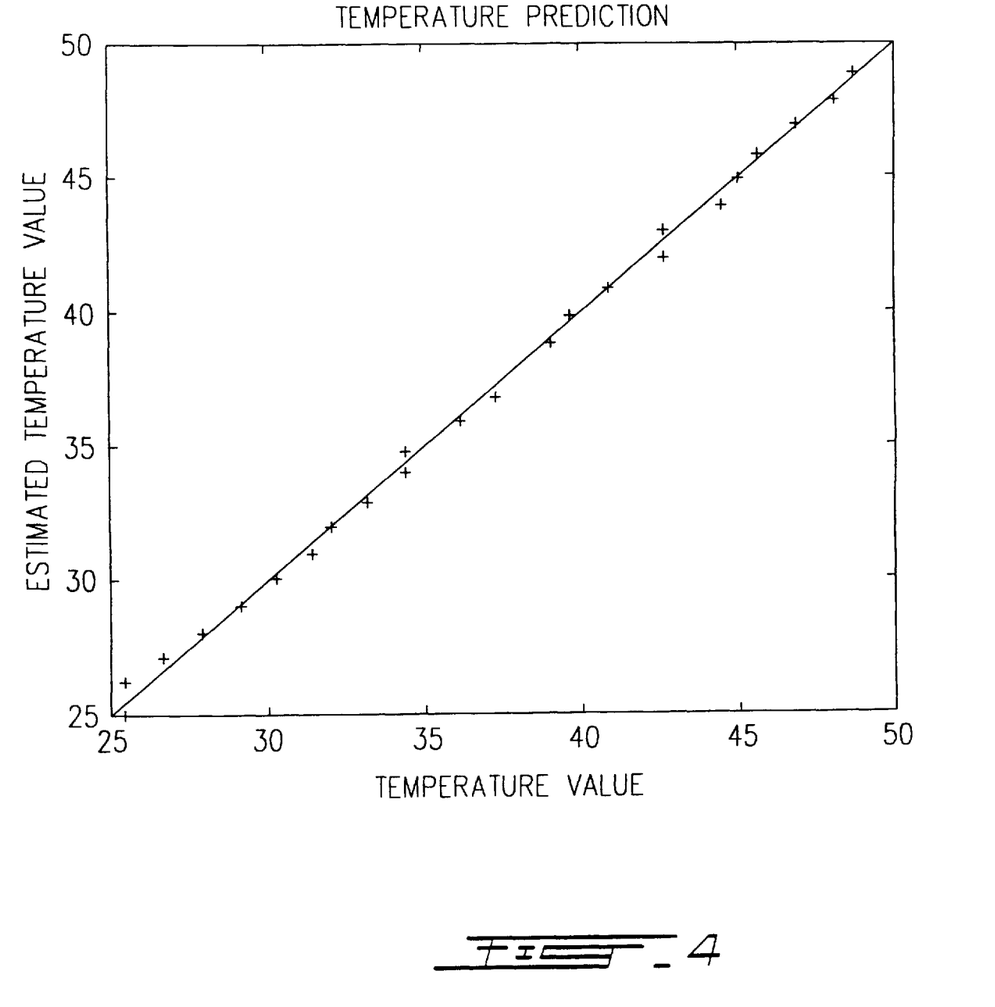
FIG. 4 is a linear plot developed from an SMLR algorithm from the data of FIG. 3.

Dependence of the near-infrared absorbance of water on temperature was determined by heating a 4 mm thick cuvette of pure water to 50° C. and measuring spectra along with associated temperatures as the sample cooled to room temperature. Examples of the measured near-infrared spectra are shown in FIG. 3. A substantial change in spectral absorbance of water is observed with changes of temperature. A PLS regression was made using the data in FIG. 3 to determine the calibration coefficients. Four independent factors were chosen in the PLS calibration. Results are plotted and a linear calibration is seen with an error of 0.1° C. FIG. 4 is typical of the linear plot derived in this manner.

Figure 5:
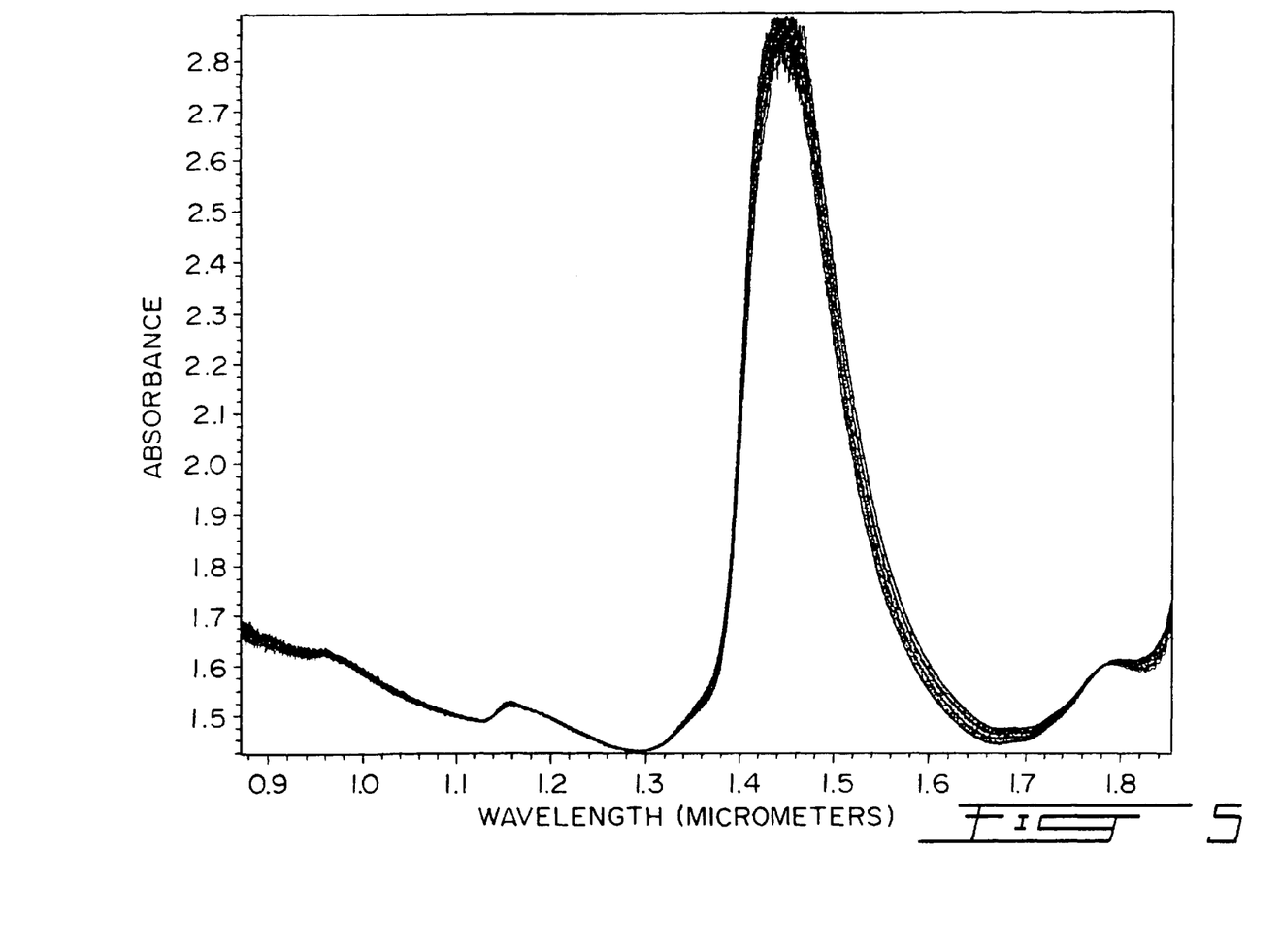
FIG. 5 shows a lung tissue spectra derived in accordance with the invention.

To confirm that temperature calibration measurements in pure water could accurately predict temperature in tissue, a series of spectral measurements were made at a 4 mm thick piece of lung tissue (bronchus) at different temperatures within the calibration region. The lung tissue spectra are shown in FIG. 5. The tissue spectra are similar to the pure water spectra, however, there is a significant baseline component present in the tissue spectra. Temperature of the lung tissue was predicted using the calibration coefficients from the pure water sample. There is significant error in the temperature measurements with some non-linearity. This is a result of the difference in the scatterers and other absorbers in the tissue spectra as compared to the pure water measurements. This would not be very useful for clinical measurements of tissue temperature, since, at best, a two point calibration would be required to adjust the estimated temperature for each tissue.

Figure 6:
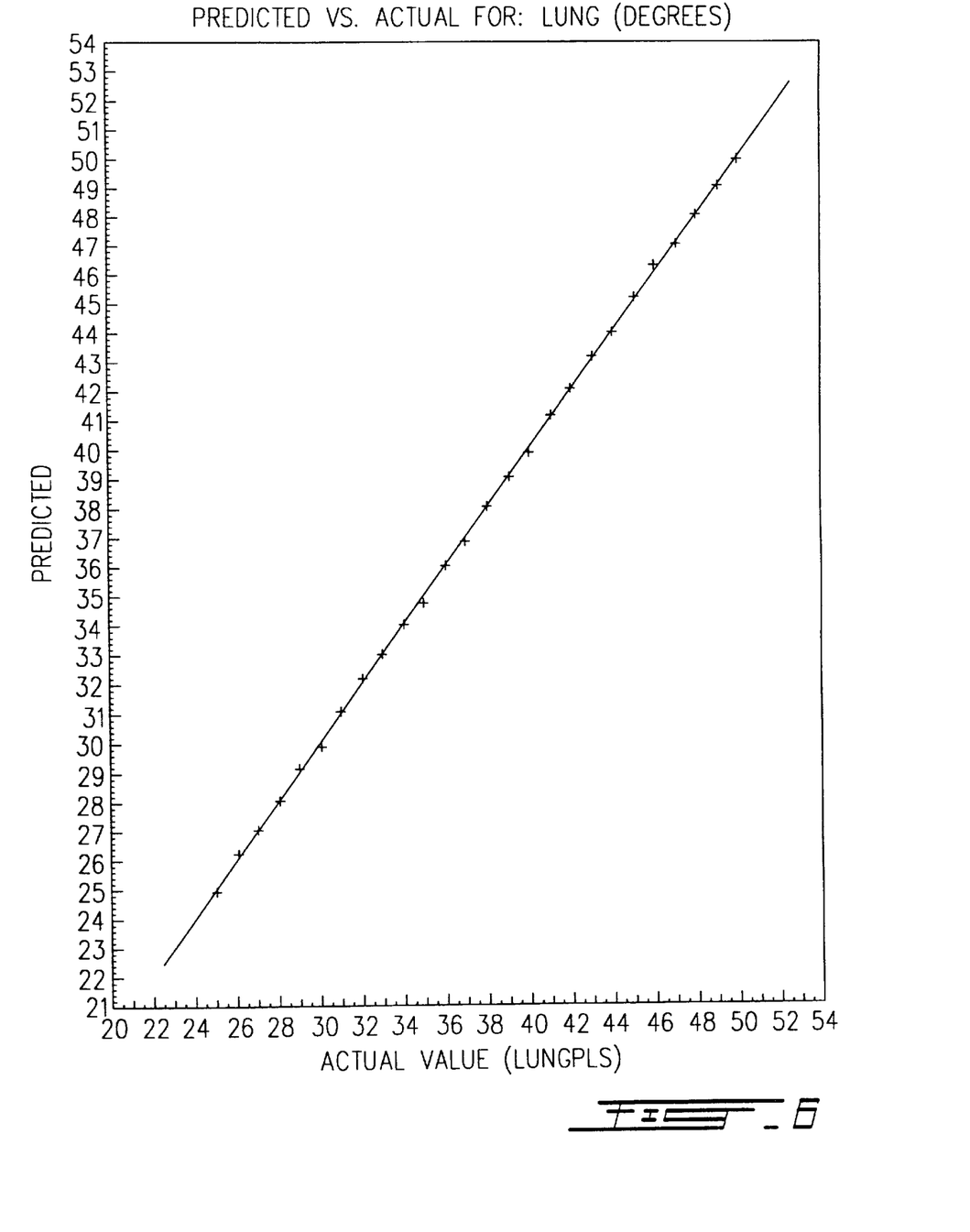
FIG. 6 is a linear plot derived from the data in FIG. 5.

However, the water within the lung tissue still changes with temperature and can be used to generated a temperature calibration. The PLS regression using the lung data in FIG. 5 was made to determine the temperature calibration coefficients. Three independent factors were chosen in the PLS calibration. Results are plotted in FIG. 6. A linear calibration is seen with an error of 0.1° C. These results are consistent with the non-scattering water measurements. Therefore, by correcting the variations with scattering, a robust temperature calibration is obtained.

Figure 7:
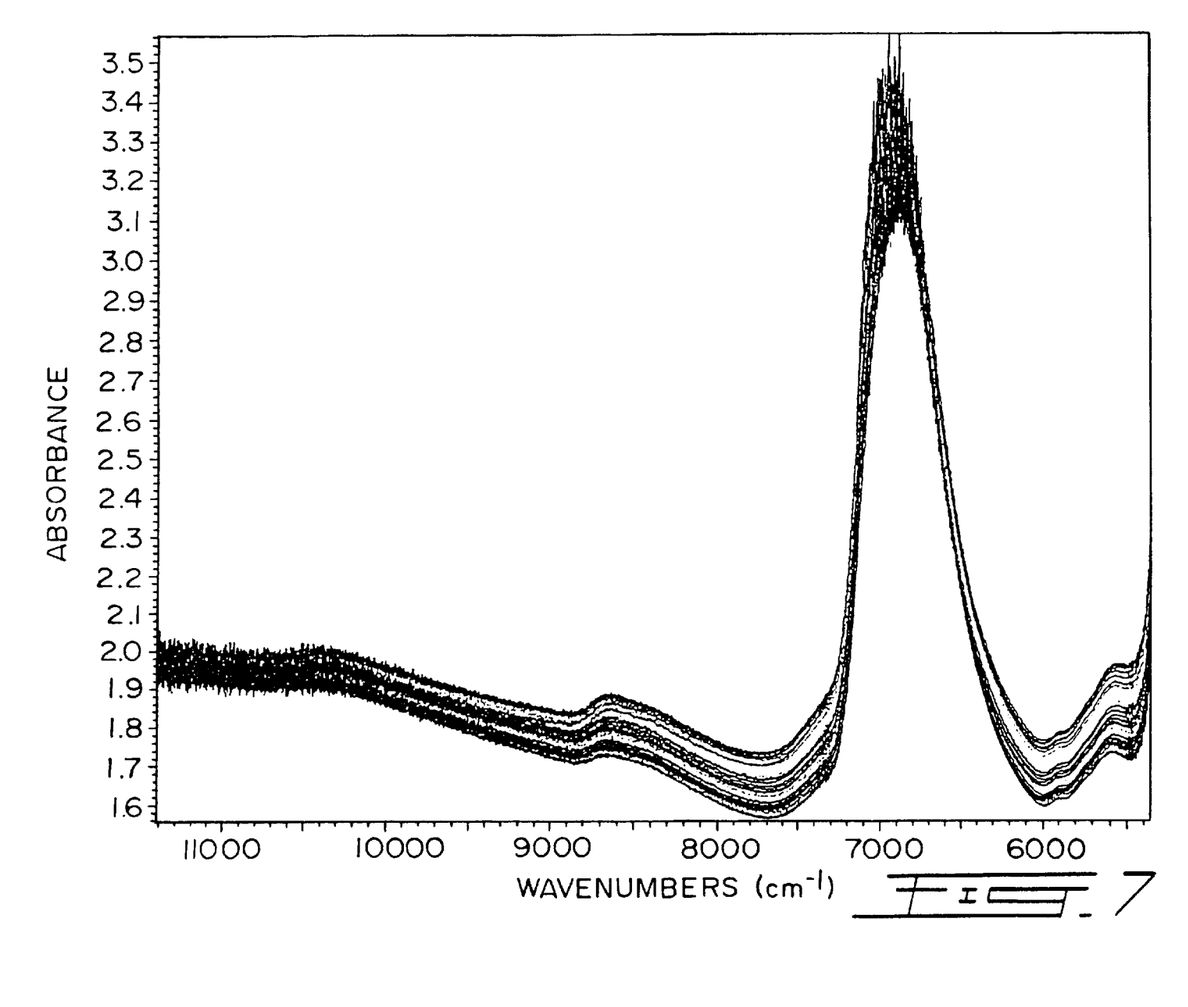
FIG. 7 is a muscle tissue spectra derived in accordance with the invention.

To demonstrate that calibration using a single tissue type was adequate for robust temperature measurements of different tissue types, a second tissue scattering sample was used. A 3 mm thick piece of excised muscle was used as the second tissue scatterer and a series of temperature correlated near-infrared spectra were taken. The measured spectra are shown in FIG. 7. Even though the muscle has significant chromogenic components in the visible spectra as compared to lung tissue, the near-infrared spectral profile is very similar. However, the different scattering characteristics of the two types of tissue result in subtle differences which influence the temperature estimation.

Figure 8:
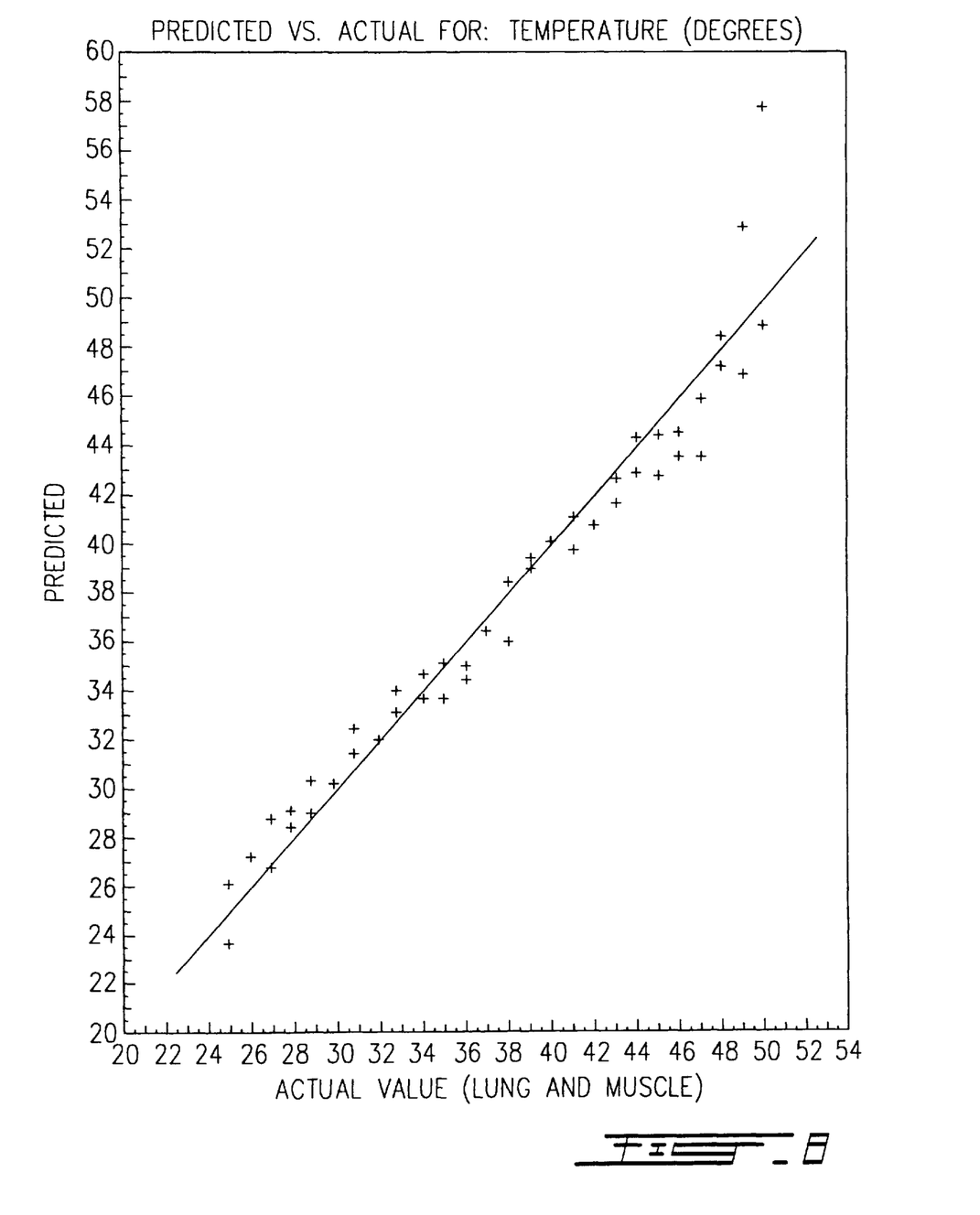
FIG. 8 is a linear plot derived from the data in FIG. 7.

One approach to the temperature calibration in variable scattering media is to construct a calibration data set which is comprised of spectral measurements made from a variety of different tissue types. As an example, when the spectral measurements were combined from both the lung and muscle into one calibration, a significant improvement in temperature measurements was possible. The calibration results are shown in FIG. 8. As is apparent, the temperature measurements are now fairly accurate. The mean error for the measurements is 1.1° C. With additional tissue types included, better calibration will be obtained.

Example 2

An apparatus of the type illustrated in FIG. 1 but replacing the bronchoscope with an optical fiber bundle was employed to measure tissue temperature in the human finger.

The system consists of an intensity stabilized tungsten-halogen light source illuminating the tissue through a fiber optic bundle. The diffuse reflected light from the tissue is collected by a second fiber optic bundle which is connected to the entrance of the near infrared spectrograph. The various wavelengths are dispersed in the spectrophotometer and collected by a diode array detector. The signal from each element of the detector represents the intensity of the light at a given near-infrared wavelength between 700 and 1100 nm. Digitization of the diode array is accomplished using an Insight 486-PC computer equipped with a National Instruments 16-bit, 100 khz A/D-D/A board. Controlling software for the system was written for signal intensity optimization and data acquisition in the tissue studies. Statistical analysis of the spectral data was accomplished using custom software written in the Matlab programming language. The entire multispectral analysis system is enclosed in a shock protected housing. This has allowed convenient transport of the system to the clinic.

Figure 9:
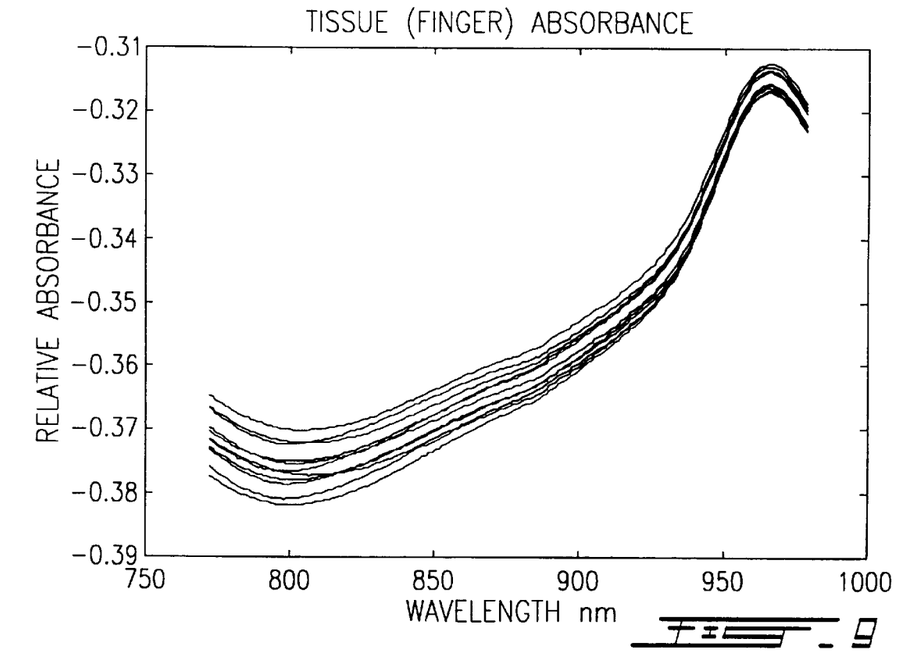
FIG. 9 is a plot of change in spectra with increase in temperature for a cooled human finger in vivo.
Figure 10:
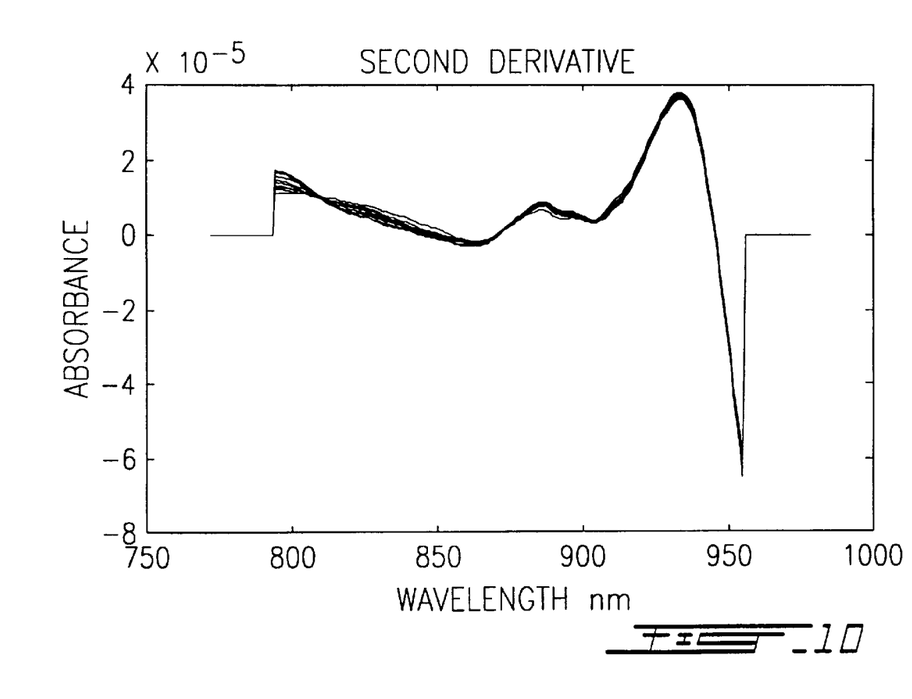
FIG. 10 is a second derivation spectral plot derived from FIG. 9.
Figure 11:
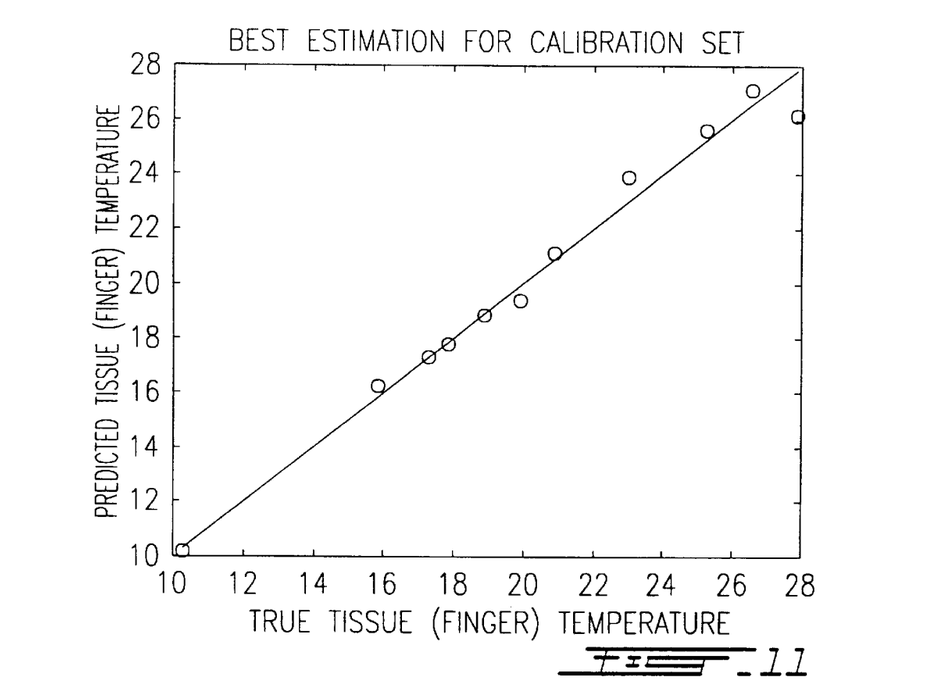
FIG. 11 is a calibration derived from the data of FIGS. 9 and 10.
Figure 12:
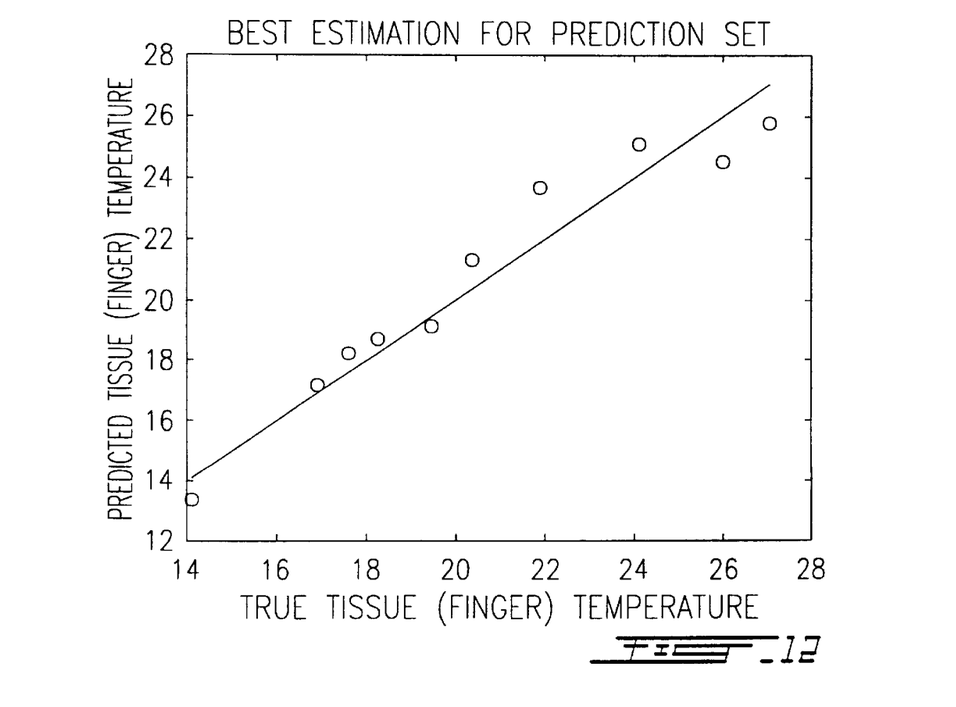
FIG. 12 is a similar calibration for a second set of test data.

Since tissue is composed of mostly water and proteins, an investigation was made to determine the relationship between the signal from water OH absorbances at different temperatures to provide a measure of the global tissue temperature. The spectral changes in the human finger were studied in vivo at different temperatures. To cool the finger from ambient body temperature (37° C.) the subject's hand was placed into a beaker of ice water. A calibrated thermocouple was taped on the subject's middle finger. When the finger reached approximately 10° C. the subject withdrew their hand and placed the fiber optic source and detector bundle next to the temperature sensor. The near infrared spectra were recorded on the finger as the tissue rewarmed using the fiber optic arrangement. During each spectral measurement the temperature in the tissue was recorded using the thermocouple. The changes in the spectra with increased temperature are shown in FIG. 9. The major changes in the spectra are an increased relative magnitude with a relative change in the OH absorbances at 810 nm and 960 nm. The change in magnitude of the signal is probably due to an increase in the amount of water as the tissue fills with blood and rewarming. The relative changes in the OH absorbances are due to the temperature change in the hydrogen bonding of water and are similar to previous in vitro measurements. To reduce the effects of the magnitude changes on the calibration and to emphasize the difference in the OH absorbance, the second derivative of the spectral were taken. The results are shown in FIG. 10. The temperature differences in the tissue spectra are clearly visible in the spectral series. Using partial least squares analysis of the spectra, calibration coefficients for the wavelengths were determined using two independent factors. Using the two factors, the temperatures of the calibration set were estimated and are shown in FIG. 11. The accuracy of the estimation is i 0.7° C. To test the system on an independent set of optical measurements, the temperature was estimated for a second "test", set of spectra from the finger. Results of the test estimation are shown in FIG. 12. The accuracy of the test set estimation is i 1.0° C. As is evident, a tight correlation between the non-invasive estimates and the measured temperature was found in both measurements. These results clearly demonstrate the feasibility of fiber optic measurement of tissue temperature by near-infrared spectroscopy.

Near-infrared measurement of water provides non-invasive temperature measurement of wet tissues. For each tissue type, the temperature calibration can be made to within the accuracy of the reference temperature measurement system. The results suggest that tissue compositional changes will influence temperature estimation. To increase the robustness of the calibration for different tissue types, a calibration model can be constructed using scattering measurements from a variety of tissues. The availability of a non-invasive system for tissue thermography would be applicable to a wide variety of physiological questions and provide information which improves the capability to determine disease and inflammation in tissue. Likewise, the accurate knowledge of tissue temperature would be helpful as a reference for other non-invasive tissue chemical measurements made in the near infrared and could be a powerful tool for non-invasive metabolic assessment.

The method may also be applied to techniques which involve measurement of other factors such as glucose concentration in which a knowledge of the temperature is needed.

Such measurements also have utility in the evaluation of other water-containing infrared radiation scattering media.

We claim:

1. A method of determining the temperature of an infrared radiation scattering medium comprising:
   a) exposing an infrared scattering medium containing a liquid which contains different hydrogen bonding at different temperatures to infrared radiation,
   b) measuring reflected infrared radiation scattered by the medium, at different wavelengths,
   c) comparing the reflected radiation with calibrated values of reflected radiation and temperature, and
   d) evaluating the temperature of the medium from the comparison,
   wherein the different wavelengths comprise wavelengths for water between 900 and 1300 nm comprising a wavelength for free OH groups and a wavelength for hydrogen-bonded OH groups.

2. A method according to claim 1; wherein said liquid is water.

3. A method according to claim 1, wherein said radiation has a near-infrared wavelength between 700 nm and 2500 nm.

4. A method according to claim 1, wherein said medium is biological tissue.

5. A method according to claim 1, wherein said medium is a paper substrate.

6. A method according to claim 1, wherein said medium is cement.

7. A method according to claim 1, wherein said medium is a clay substrate.

8. An apparatus for determining the temperature of an infrared radiation scattering medium comprising:

i) a plurality of optical fibers effective to transmit infrared radiation from a source to a scattering medium and to transmit reflected scattered radiation from said scattering medium, ii) a source of infrared radiation operatively associated with said fibers for transmission of infrared radiation, iii) detector means adapted to receive reflected radiation for multiple wavelengths from said optical fibers and issue signals responsive thereto, iv) evaluating means for receiving said signals and determining the temperature of the scattering medium therefrom, said evaluating means being adapted to compare the received signals with signals corresponding to calibrated values of reflected radiation and temperature, and v) an endoscope, said plurality of optical fibers being associated with said endoscope wherein said detector comprises filters for said multiple wavelengths, said filters being for hydrogen bonding and free OH group wavelengths in the range of 900 to 1300 nm.

9. An apparatus according to claim 8, wherein said filters comprise a first filter for a wavelength in the range of 1100 to 1300 nm for free OH groups and a second filter for a wavelength in the range of 900 to 1100 nm for hydrogen-bonded OH groups.

10. An apparatus according to claim 8 wherein said detector means includes a near-infrared spectrophotometer and a photodiode array detector adapted to issue the signals.

11. An apparatus according to claim 8 wherein said detector includes a diffraction grating to disperse said multiple wavelengths and a photodiode array adapted to issue the signals responsive to the dispersed wavelengths.

* * * * *